US011680899B2

(12) United States Patent
    Rowe

(10) Patent No.: US 11,680,899 B2
(45) Date of Patent: Jun. 20, 2023

(54) LASER DISPERSION SPECTROSCOPY FOR BOREHOLE ANALYSIS

(71) Applicant: Halliburton Energy Services, Inc., Houston, TX (US)

(72) Inventor: Mathew Dennis Rowe, Spring, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 359 days.

(21) Appl. No.: 16/903,211

(22) Filed: Jun. 16, 2020

(65) Prior Publication Data

US 2021/0389239 A1    Dec. 16, 2021

(51) Int. Cl.
    *G01J 3/30*      (2006.01)
    *G01N 21/39*    (2006.01)
    (Continued)

(52) U.S. Cl.
    CPC ........... *G01N 21/39* (2013.01); *E21B 21/066* (2013.01); *E21B 43/35* (2020.05); *E21B 49/005* (2013.01);
    (Continued)

(58) Field of Classification Search
    CPC ........ G01N 21/39; G01N 21/17; G01N 21/41; G01N 1/28; G01N 1/286; G01N 1/34;
    (Continued)

(56) References Cited

U.S. PATENT DOCUMENTS

| 4,163,382 A | 8/1979 | Amer |
| 7,520,158 B2 | 4/2009 | DiFoggio |

(Continued)

FOREIGN PATENT DOCUMENTS

| EP | 1896690 B1 | 12/2011 |
| EP | 3156587 A1 | 4/2017 |
| WO | 2018229469 A1 | 12/2018 |

OTHER PUBLICATIONS

G. Plant, A. Hangauer, M. Nikodem, and G. Wysocki, "Recent Advances in Chemical Detection with Chirped Laser Dispersion Spectroscopy," in Imaging and Applied Optics 2014, OSA Technical Digest (online) (Optica Publishing Group, 2014), paper LW1D.1 (Year: 2014).*

(Continued)

*Primary Examiner* — Tarifur R Chowdhury
*Assistant Examiner* — Jonathon Cook
(74) *Attorney, Agent, or Firm* — Benjamin Ford; Parker Justiss, P.C.

(57) ABSTRACT

This disclosure presents a process and system to determine characteristics of a subterranean formation proximate a borehole. Borehole material is typically pumped from the borehole, though borehole material can be used within the borehole as well. Extracted material of interest is collected from the borehole material and prepared for analyzation. Typically, the preparation can be a separation process, a filtering process, a moisture removal process, a pressure control process, a flow control process, a cleaning process, and other preparation processes. The prepared extracted material is placed in a laser dispersion spectroscopy device (LDS) where measurements can be taken. A LDS analyzer can generate results utilizing the measurements, where the results of the extracted material can include one or more of composition parameters, alkene parameters, and signature change parameters. The results can be communicated to other systems and processes to be used as inputs into well site operation plans and decisions.

25 Claims, 7 Drawing Sheets

(51) Int. Cl.
*G01N 33/24* (2006.01)
*G01N 1/28* (2006.01)
*E21B 49/00* (2006.01)
*E21B 21/06* (2006.01)
*E21B 43/34* (2006.01)
*G01N 1/34* (2006.01)

(52) U.S. Cl.
CPC ............... *G01N 1/286* (2013.01); *G01N 1/34* (2013.01); *G01N 33/241* (2013.01); *G01N 2001/2866* (2013.01)

(58) Field of Classification Search
CPC ............. G01N 33/241; G01N 33/2823; G01N 2001/2866; E21B 43/35; E21B 21/066; E21B 49/005
See application file for complete search history.

(56) References Cited

U.S. PATENT DOCUMENTS

| | | |
|---|---|---|
| 2008/0078544 A1 | 4/2008 | Christian et al. |
| 2009/0156877 A1 | 6/2009 | Newman et al. |
| 2011/0043202 A1 | 2/2011 | Fransson et al. |
| 2012/0225489 A1 | 9/2012 | Yepez et al. |
| 2013/0011872 A1 | 1/2013 | Gabriel |
| 2015/0322781 A1 | 11/2015 | Pelletier et al. |
| 2016/0115786 A1 | 4/2016 | Breviere et al. |
| 2017/0045491 A1 | 2/2017 | Karoum et al. |
| 2017/0362926 A1 | 12/2017 | DiFoggio |
| 2018/0171786 A1 | 6/2018 | Kasprzykowski et al. |
| 2019/0059739 A1 | 2/2019 | Abe |
| 2019/0145935 A1 | 5/2019 | Csutak et al. |
| 2019/0257751 A1* | 8/2019 | Plant ..................... G01J 3/433 |
| 2019/0390524 A1 | 12/2019 | Bentamy et al. |
| 2020/0003694 A1 | 1/2020 | Sauerer et al. |

OTHER PUBLICATIONS

Michal Nikodem, Clinton Smith, Damien Weidmann, Gerard Wysocki, "Remote mid-infrared sensing using chirped laser dispersion spectroscopy," Proc. SPIE 8024, Advanced Environmental, Chemical, and Biological Sensing Technologies VIII, 80240F (May 26, 2011) (Year: 2011).*

Mohan, et al.; "Crack detection using image processing: A critical review and analysis"; Elsevier; Alexandria University Alexandria Engineering Journal; www.elsevier.com/locate/aej;www.sciencedirect.com; Nov. 29, 2016; 12 pgs.

Mi, et al.; "Probing of laser-induced crack modulation by laser-monitored surface waves and surface skimming bulk waves"; JASA Express Letters; Acoustical Society of America; Nov. 21, 2011; 6 pgs.

* cited by examiner

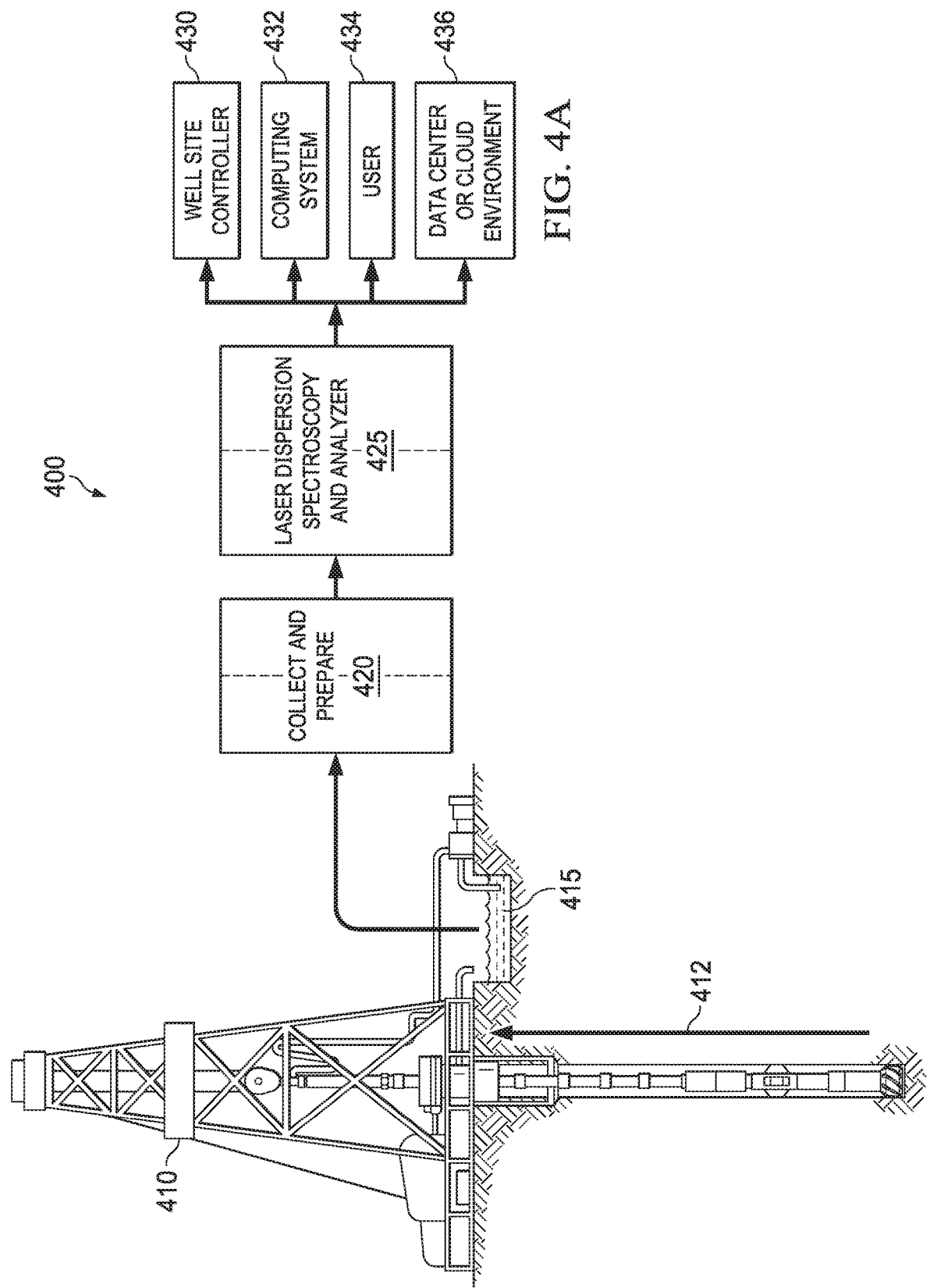

LASER DISPERSION SPECTROSCOPY FOR BOREHOLE ANALYSIS

TECHNICAL FIELD

This application is directed, in general, to utilizing a laser dispersion spectroscopy device with borehole material and, more specifically, to determining subterranean formation characteristics.

BACKGROUND

In the hydrocarbon industry, parameters regarding a subterranean formation surrounding a borehole is information that may be used as inputs to decisions and operation plans in furthering development of the well site. The parameters of the subterranean formation can include fracture information, composition, permeability, porosity and other characteristics. The industry uses a variety of sensors to collect measurements that are then analyzed and used to generate the subterranean formation parameters, such as seismic sensors, electromagnetic sensors, acoustic sensors, thermal sensors, chemical sensors, and other sensor types. The data gained from these sensors may vary as to quality and ease of obtaining the measurements. A method of determining these characteristics with higher quality and accuracy would be beneficial.

SUMMARY

In one aspect, a method is disclosed. In one embodiment the method includes (1) collecting extracted material from a location in a subterranean formation, wherein the location is proximate a position of a hydrocarbon operation within a borehole, (2) preparing the extracted material, wherein extraneous material is removed, (3) putting the extracted material into a laser dispersion spectroscopy (LDS) device, (4) initiating a LDS process utilizing the extracted material, and (5) generating results from an analyzation of the LDS process.

In another aspect, a system to analyze extracted material, extracted from a location within a borehole is disclosed. In one embodiment the system includes (1) an extracted material collector, capable of collecting the extracted material to be analyzed from borehole material, (2) an extracted material preparer, capable of receiving the extracted material from the extracted material collector and capable of cleaning, separating, isolating, and altering the extracted material to prepare the extracted material for analysis, (3) a LDS device, capable of receiving the extracted material from the extracted material preparer and capable of performing a LDS process on the extracted material, and (4) a LDS analyzer, capable of producing results from an output of the LDS device.

In another aspect, a computer program product having a series of operating instructions stored on a non-transitory computer-readable medium that directs a data processing apparatus when executed thereby to perform operations to analyze extracted material is disclosed. In one embodiment, the operations include (1) directing a collecting of the extracted material from a location in a subterranean formation, wherein the location is proximate a position of hydrocarbon operations within a borehole, (2) instructing a preparing of the extracted material, wherein extraneous material is removed, (3) initiating a putting of the extracted material into a LDS device, (4) executing a LDS process utilizing the extracted material, (5) analyzing results from the LDS process, and (6) communicating the results to one or more other systems.

BRIEF DESCRIPTION

Reference is now made to the following descriptions taken in conjunction with the accompanying drawings, in which:

FIG. 4A is an illustration of a block diagram of an example laser dispersion spectroscopy (LDS) analyzation system located at a surface of a well site;

DETAILED DESCRIPTION

Figure 1:
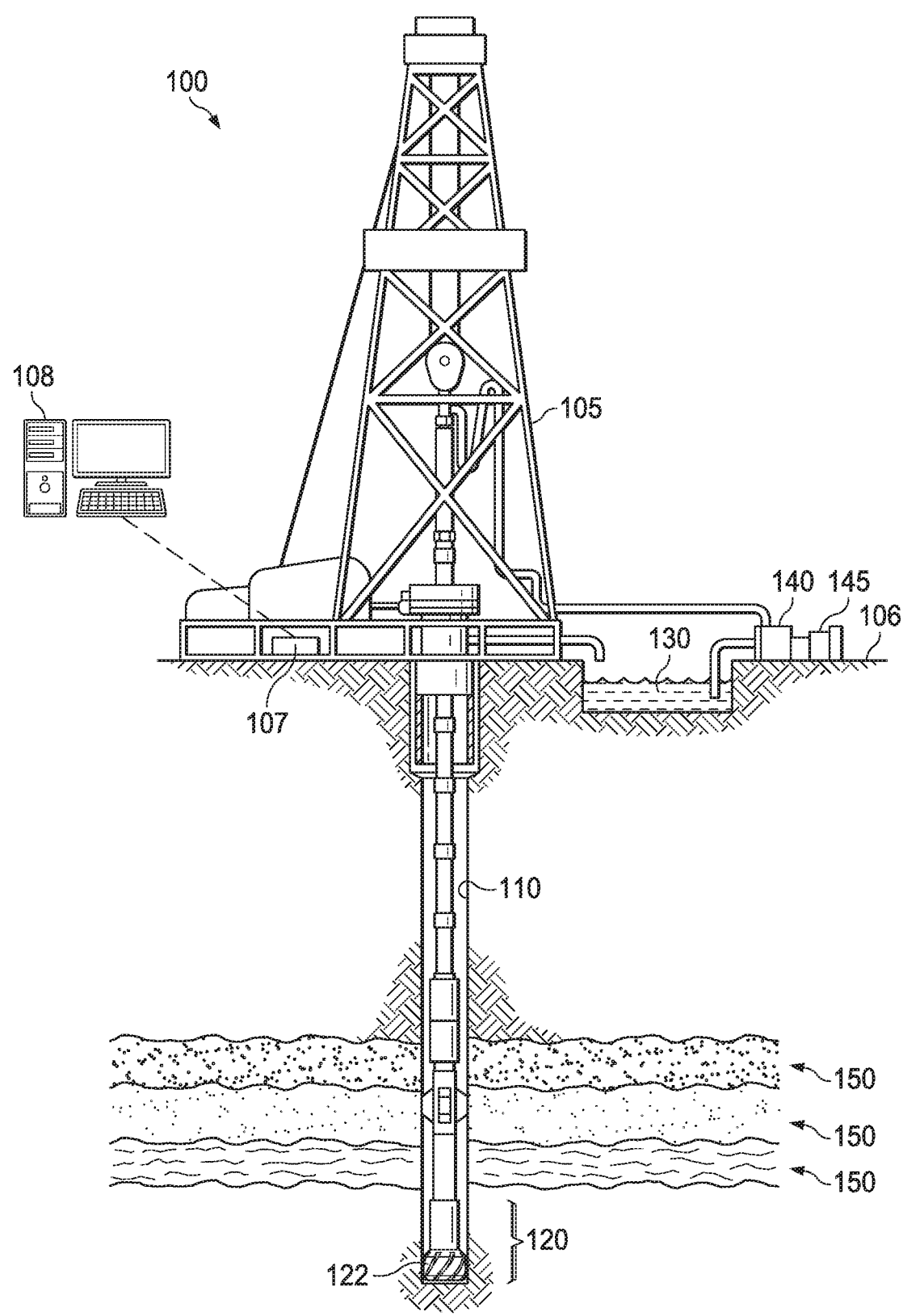
FIG. 1 is an illustration of a diagram of an example well system.

In the hydrocarbon production industry, users, such as well operators or engineers, can use information regarding the subterranean formation around a borehole to make further adjustments to the well site operations. In a drilling operation, such as for a production well, intercept well, relief well, and other well types, being able to determine the composition of the surrounding subterranean formation can be useful as inputs into a well site operation plan. In casing operations, the placement of casing, the thickness used, and other casing factors can be determined by the characteristics of the surrounding subterranean formation.

Sampling cuttings from drilling operations may not reveal the natural characteristics of the subterranean formation as drilling operations can cause a change in the sampled cuttings due to action of the drill bit. Corrections to the altered characteristics are needed to more accurately determine the characteristics of the subterranean formation. Using a comparison of a sampled core, sidewall core, or subterranean formation image to the collected cuttings, corrections can be made to the determined composition characteristics and the effects of the drill bit on the composition can be compensated. In some aspects, formation plane orientation can be determined from the cuttings.

Other subterranean formation characteristics can include a determination of the composition of the subterranean formation and whether it contains organic or inorganic material. In some aspects, during drilling operations, an unsaturated hydrocarbon change or a signature change can be detected and an alert sent to the users indicating the changed condition downhole. A signature change, e.g., a phase or composition signature change, can be, for example, a gas/liquid transition, or the increase or decrease of water in the borehole.

In the industry today, there are several methods utilized to obtain the various subterranean formation characteristics, such as seismic sensors, electromagnetic sensors, thermal sensors, chemical sensors, acoustic sensors, radiation sensors, and other sensor types. In some aspects, visual inspection of cuttings can be used. The ability to take sensor readings downhole can vary as to effectiveness, such as some sensors operate while the drilling operations cease. Other restrictions relate to the power needed by the sensors and the data rates needed to send collected measurements to a surface system.

This disclosure presents a laser dispersion spectroscopy (LDS) system that can determine several subterranean formation characteristics. The disclosed system can be performed at a surface location proximate the well site where power consumption of the sensors and data transmission rates can be maintained at appropriate levels. The disclosed system can be performed at regular time intervals, where the time interval can be nearly continuous or at a specified time interval. In some aspects, the LDS system can be performed downhole, where the LDS device is located proximate downhole tools, such as power supplies, transceivers, and other equipment, such as drill bits.

Cuttings can be collected from the subterranean formation, such as extracted from the drilling mud, hydraulic fracturing fluid, chemical fracturing fluid, and other fluids located in the borehole or pumped to a surface location. The cuttings can be prepared, such as cleaned, drained of fluid, filtered, separated, and otherwise processed for further analysis, such as removing extraneous material.

In some aspects, the LDS device can utilize multiple generated energy wave lengths to determine composition of the extracted material by detecting the energy wave dispersion, such as a mineral composition, a molecular composition, or an organic composition. The increased sensitivity and selectivity with broad linearity can improve upon results produced by current gas chromatography and liquid phase detectors. In some aspects, the disclosed processes can be applied for gas phase analysis (utilizing a photoacoustic spectroscopy gas phase device), liquid phase analysis (utilizing a photoacoustic spectroscopy liquid phase device), solid phase analysis (utilizing a photoacoustic spectroscopy solid phase device), and isotropic analysis (utilizing a photoacoustic spectroscopy isotropic device) in the gas phase. The energy waves can be for example, sound waves, infrared waves, visible light waves, gamma waves, x-rays, and other energy wave lengths.

In some aspects, the LDS device can be utilized in conjunction with selective physical-chemical separation techniques (utilizing a physical-chemical separation device), such as isotropic testing systems. In some aspects, the LDS device can be utilized in combination with a gas chromatography (GC) system, such as a GC combustion system or other types of GC systems. The GC system can be part of the LDS device, a separate device included with the LDS device, or a separate device proximate the LDS device. In some aspects, the LDS device can be utilized in combination with a liquid chromatography (LC) system, such as a LC combustion system or other types of LC systems. The LC system can be part of the LDS device, a separate device included with the LDS device, or a separate device proximate the LDS device.

Turning now to the figures, FIG. 1 is an illustration of a diagram of an example well system 100 using a LDS device for analyzing cuttings extracted from a downhole location where a hydrocarbon operation is being conducted, for example, a drilling system, a logging while drilling (LWD) system, a measuring while drilling (MWD) system, a seismic while drilling (SWD) system, a telemetry while drilling system, an extraction system, a formation evaluation system, a fluids evaluation system, a production system, a wireline system with a pump, and other hydrocarbon well systems such as relief wells and intercept wells. Well system 100 includes a derrick 105, a well site controller 107, and a computing system 108. Well site controller 107 includes a processor and a memory and is configured to direct operation of well system 100. Derrick 105 is located at a surface 106.

Extending below derrick 105 is a borehole 110 with downhole tools 120 at the end of a drill string. Downhole tools 120 can include various downhole tools and bottom hole assemblies (BHA), such as drilling bit 122. Other components of downhole tools 120 can be present, such as a local power supply (e.g., generators, batteries, or capacitors), telemetry systems, sensors, transceivers, and control systems. Borehole 110 is surrounded by subterranean formation 150.

The drilling mud pumped out of borehole 110 can be stored in a mud storage 130. Extracted material from mud storage 130 can be collected and moved to a extracted material preparer 140. The extracted material can be cleaned, separated, have fluid drained, and other preparation functions, such as pulverizing solids or converting gases to carbon dioxide. After preparation, the extracted material can be moved to a LDS device 145 where a LDS process can be performed on the extracted material. Results can be generated by LDS device 145 or by another system, such as well site controller 107 or computing system 108. LDS device 145 can be one or more devices. For example. a separate LDS device can be utilized for the phase state of the extracted material, such as a gas phase device, a liquid phase device, a solid phase device, and an isotropic device.

Well site controller 107 or computing system 108 which can be communicatively coupled to well site controller 107, can be utilized to communicate with downhole tools 120, such as sending and receiving telemetry, data, instructions, and other information. Computing system 108 can be proximate well site controller 107 or be a distance away, such as in a cloud environment, a data center, a lab, or a corporate office. Computing system 108 can be a laptop, smartphone, PDA, server, desktop computer, cloud computing system, other computing systems, or a combination thereof, that are operable to perform the process and methods described herein. Well site operators, engineers, and other personnel can send and receive data, instructions, measurements, and other information by various conventional means with computing system 108 or well site controller 107.

Well site controller 107 or computing system 108 can also communicate with extracted material preparer 140 and LDS device 145 to direct operations and receive the measured data and results. For example, LDS device 145 can perform an analysis on extracted material and transmit the results to well site controller 107 or computing system 108. In an alternative aspect, the measurements taken by LDS device 145 can be communicated to well site controller 107 or computing system 108 and the results generated in one or more of those respective systems.

In FIG. 1, the extracted material preparer 140 and LDS device 145 is represented at a surface location proximate derrick 105. In other aspects, extracted material preparer 140 and LDS device 145 can be located downhole as part of downhole tools 120. In this aspect, the measurements taken or the generated results can be communicated uphole to well site controller 107 or computing system 108. A user or well site controller 107 can utilize the generated results to direct further operations of the well system 100, such as adjusting drilling operations, fluid flow, rate, and composition, and adjusting a well site operation plan.

Figure 2:
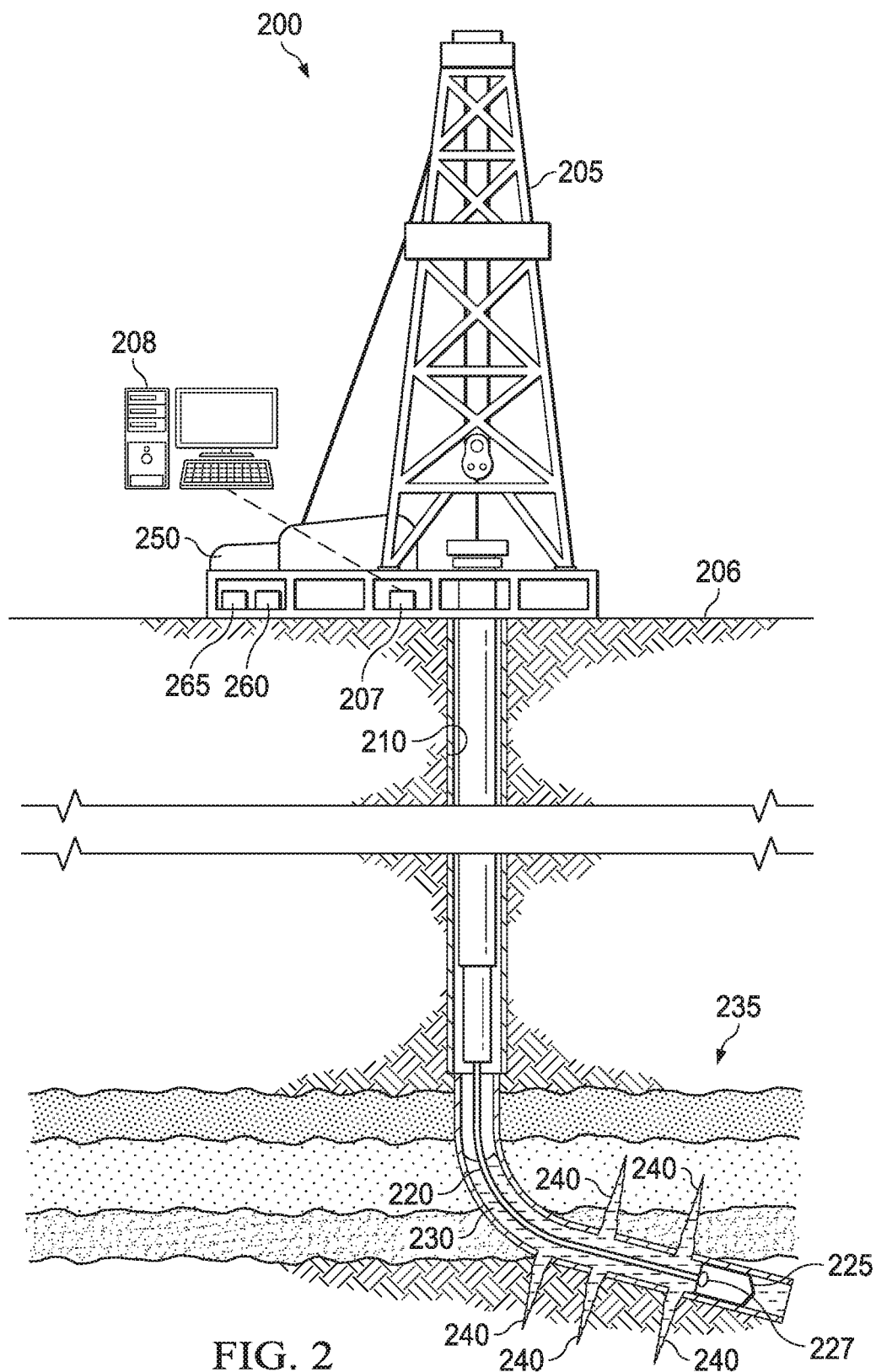
FIG. 2 is an illustration of a diagram of an example hydraulic fracturing well system.

FIG. 2 is an illustration of a diagram of an example hydraulic fracturing (HF) well system 200 undergoing a hydrocarbon operation. HF well system 200 demonstrates a nearly horizontal borehole undergoing a hydraulic fracturing operation. In other aspects, HF well system 200 can be other types of HF well systems or chemical fracturing operation well systems.

HF well system 200 includes surface well equipment 205 located at a surface 206, well site control equipment 207, and a computing system 208. In some aspects, well site control equipment 207 is communicatively connected to separate computing system 208, for example, a server, data center, cloud service, tablet, laptop, smartphone, or other types of computing systems. Computing system 208 can be located proximate to well site control equipment 207 or located a distance from well site control equipment 207, and can be utilized by a well system engineer and operator to transceive data, instructions, and other information with an extracted material preparer 260 and a LDS device 265. A hydraulic fluid reservoir 250 can store fluid pumped out of borehole 210. Extracted material contained in the hydraulic fluid can be collected and moved to extracted material preparer 260 where the extracted material can be cleaned, drained, separated, or otherwise prepared, such as described for extracted material preparer 140.

Extending below surface 206 from surface well equipment 205 is a borehole 210. Borehole 210 can have zero or more cased sections and a bottom section that is cased or uncased. Inserted into borehole 210 is a fluid pipe 220. The bottom portion of fluid pipe 220 has the capability of releasing downhole material 230, such as carrier fluid with diverter material, from fluid pipe 220 to subterranean formations 235 containing fractures 240. The release of downhole material 230 can be by sliding sleeves, valves, perforations in fluid pipe 220, or by other release means. At the end of fluid pipe 220 is an end of pipe assembly 225, which can include one or more downhole tools 227 or an end cap assembly.

LDS device 265 can communicate measurements or analyzed results to well site control equipment 207 or computing system 208. Extracted material preparer 260 and LDS device 265, which can be one or more of the LDS devices as described for LDS device 145, can receive inputs from a user, well site control equipment 207, or computing system 208. The inputs can direct operations, such as specifying a time interval to perform the analyzation, a verification time interval, or a calibration time interval. In some aspects, the inputs can include reference calibrations, locations within the borehole to perform the LDS analysis, core sample data (such as collected by downhole tools 227), and other inputs to direct operations such as specifying the utilization of an algorithm or a machine learning process. In some aspects, extracted material preparer 260 and LDS device 265 can be located with downhole tools 227.

Figure 3:
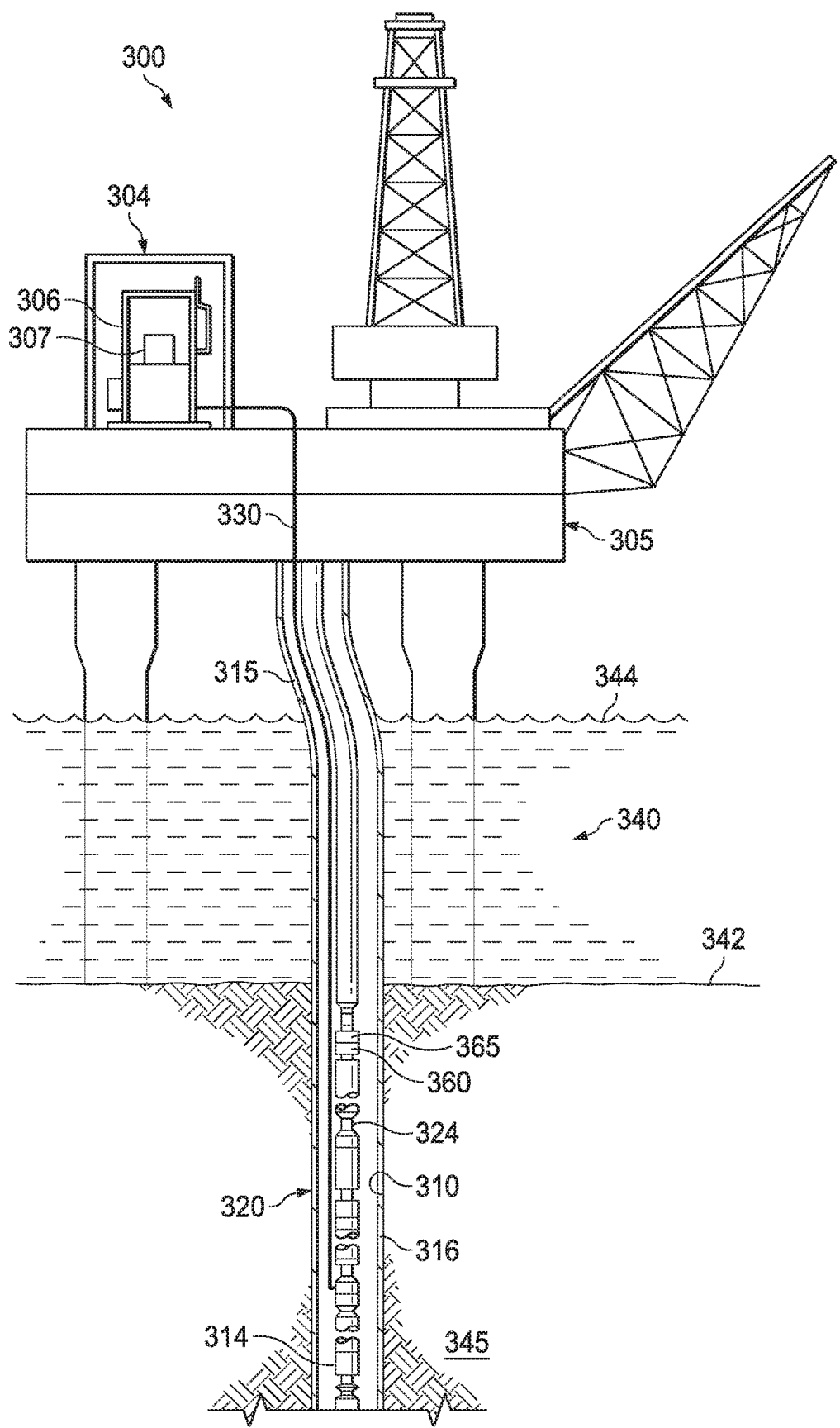
FIG. 3 is an illustration of a diagram of an example offshore well system.

FIG. 3 is an illustration of a diagram of an example offshore well system 300, where an electric submersible pump (ESP) assembly 320 is placed downhole in a borehole 310 below a body of water 340, such as an ocean or sea. Borehole 310, protected by casing, screens, or other structures, is surrounded by subterranean formation 345. ESP assembly 320 can also be used for onshore operations. ESP assembly 320 includes a well controller 307 (for example, to act as a speed and communications controller of ESP assembly 320), an ESP motor 314, and an ESP pump 324.

Well controller 307 is placed in a cabinet 306 inside a control room 304 on an offshore platform 305, such as an oil rig, above water surface 344. Well controller 307 is configured to adjust the operations of ESP motor 314 to improve well productivity. In the illustrated aspect, ESP motor 314 is a two-pole, three-phase squirrel cage induction motor that operates to turn ESP pump 324. ESP motor 314 is located near the bottom of ESP assembly 320, just above downhole sensors within borehole 310. A power/communication cable 330 extends from well controller 307 to ESP motor 314.

In some aspects, ESP pump 324 can be a horizontal surface pump, a progressive cavity pump, a subsurface compressor system, or an electric submersible progressive cavity pump. A motor seal section and intake section may extend between ESP motor 314 and ESP pump 324. A riser 315 separates ESP assembly 320 from water 340 until sub-surface 342 is encountered, and a casing 316 can separate borehole 310 from subterranean formation 345 at and below sub-surface 342. Perforations in casing 316 can allow the fluid of interest from subterranean formation 345 to enter borehole 310.

Offshore well system 300 is demonstrating an example where an extracted material preparer 360 and LDS device 365 are located downhole as part of ESP assembly 320. As cuttings, through mud or fluid, is pumped up to the surface, the LDS borehole analyzer system can collect the cuttings and fluid and process them as described in well system 100 and HF well system 200. The measurements taken and the analyzed results can be communicated to well controller 307. In other aspects, extracted material preparer 360 and LDS device 365 can be located on offshore platform 305.

FIGS. 1 and 2 depict onshore operations. Those skilled in the art will understand that the disclosure is equally well suited for use in offshore operations. FIGS. 1, 2, and 3 depict specific borehole configurations, those skilled in the art will understand that the disclosure is equally well suited for use in boreholes having other orientations including vertical boreholes, horizontal boreholes, slanted boreholes, multilateral boreholes, and other borehole types.

FIG. 4A is an illustration of a block diagram of an example LDS analyzation system 400 located at a surface of a well site. LDS analyzation system 400 can be used to analyze material extracted from a down hole location, such as from mud, hydraulic fracturing fluid, chemical fracturing fluid, and other fluids and materials pumped to the surface of the well site. A well system 410 can pump one or more fluids and materials from a downhole location as indicated along directional flow arrow 412. The fluid and materials can be pumped to a storage area 415.

The extracted material of interest can be extracted from storage area 415, such as using an extracted material collector 420. The extracted material can be in any phase state, such as a gas, liquid, or solid. The extraction process can vary for each type of phase state to minimize a loss of material during the extraction process. In this example, extracted material collector 420 is further capable of preparing the extracted material. In some aspects, the collection and preparation functions can be separated into different devices, as indicted by the dotted line dividing extracted material collector 420.

For the preparation function, the extracted material can be prepared depending on the phase state. For example, a gas can be separated from the material that traps the gas and separated from other gasses trapped in the material. The preparation can be a separation process, a filtering process, a dilution process, a moisture removal process, a pressure control process, a flow control process, a flow rate adjustment process, a cleaning process, an isolating process, a removing extraneous material process, an additional support gases process, and other preparation processes. In some aspects, the gas can be converted to carbon dioxide, such as through a combustion process. A liquid can be separated from other material in the collected material, and similar to the gas state, can be filtered, have its pressure adjusted, have its flow adjusted, have additional fluids added, and other preparation steps. A solid, in addition to the preparation steps described for the other phase states, can be cleaned, drained of fluid, pulverized, and have other preparation steps. In some aspects, organic extracted material can be prepared differently than inorganic extracted material.

Extracted material collector 420 can be one or more devices, such as a separate device to handle each of the phase states or type of extracted material. The prepared extracted material can then be moved to a LDS device 425. In some aspects LDS device 425 can include LDS analyzer and in other aspects, LDS analyzer can be a separate device or computing system, as shown by the dotted line in LDS device 425. There can be more than one LDS device 425 to analyze different types of extracted material or to perform different types of analysis. In some aspects, LDS device 425 can include one or more of a GC system, a GC combustion system, a LC system, or a LC combustion system. In some aspects, LDS device 425 can include other types of physical-chemical separation techniques.

The measurements collected by LDS device 425 can then be analyzed by a LDS analyzer that is part of LDS device 425 or is performed by a separate computing system. In some aspects, the separate computing system can be a well site controller, such as well site controller 430, a computing system, such as computing system 432, or other computing systems.

The LDS analyzer can perform one or more operations to produce a result that can be further communicated to other systems or users. For example, the results can be transmitted, using a results transmitter, to well site controller 430, computing system 432, a user 434, or a data center 436 which can be a cloud environment. In some aspects, the results can be transmitted to a downhole tool controller, a well site operation plan system, or other computing system. The well site controller or well site operation plan can utilize the results to determine next steps, or to adjust plans or operations. LDS analyzation system 400 is shown as a demonstration of a functional implementation. Extracted material collector 420 and LDS device 425 can be implemented using one or more devices to handle the described functions of each device.

The results that are produced can vary with the type of analysis being performed and the type of extracted material being analyzed. In some aspects, a spectral deconvolution process can be performed based on reference standards or can utilize an artificial intelligence process such as machine learning algorithms or deep neural networks. The spectral deconvolution process can determine the composition of the extracted material. In some aspects, the spectral deconvolution process can determine if the extracted material is organic or inorganic.

In some aspects, such as when the extracted material is a solid, a vitrinite reflectance can be performed for organic composition analysis to generate a result including a vitrinite reflectance parameter. In some aspects, an isotropic analysis can be performed on the extracted material, for example, to determine the amount of methane containing various particles that is detected. In gas phase analysis or isotropic analysis, the target gas or target liquid released from the extracted material can be analyzed at low levels of concentration to determine the measurements. In some aspects, the results can include a status of the system.

In some aspects, the analysis can determine if unsaturated linear hydrocarbon, e.g., alkenes, compositions are present. An alert, e.g., an unsaturated hydrocarbon message, can be output when a target quantity of unsaturated hydrocarbons is met or exceeded. This can be an indicator of inefficient drilling and therefore can be used as an input to adjust drilling operations.

In some aspects, a phase signature or composition signature can change over time for subsequent samples of extracted material. For example, the process can detect a drop in oil and an increase in water in the extracted material, or a gas can now be detected as occurring in a liquid state. Once the phase or composition signature is ascertained for the extracted material, the signature can be compared to one or more previously collected samples of extracted material. When the signature change meets or exceeds a specified signature change parameter, then a signature change message can be output indicating the change. For example, the signature change parameter can indicate that an oil-water ratio should change by at least a specified percentage before a signature change message is communicated. The signature change message can be used as an input to direct further operations of the well site.

In some aspects, if a selected reference peak shifts or if a specified verification time interval has elapsed, the LDS analyzer can direct LDS device 425 to perform a calibration verification, for example, using a calibration gas or liquid, e.g., a known sample. In some aspects, if the verification of calibration fails or if a specified calibration time interval elapses, LDS device 425 can perform a calibration process. A calibration parameter can be included in the communicated results.

Figure 4B:
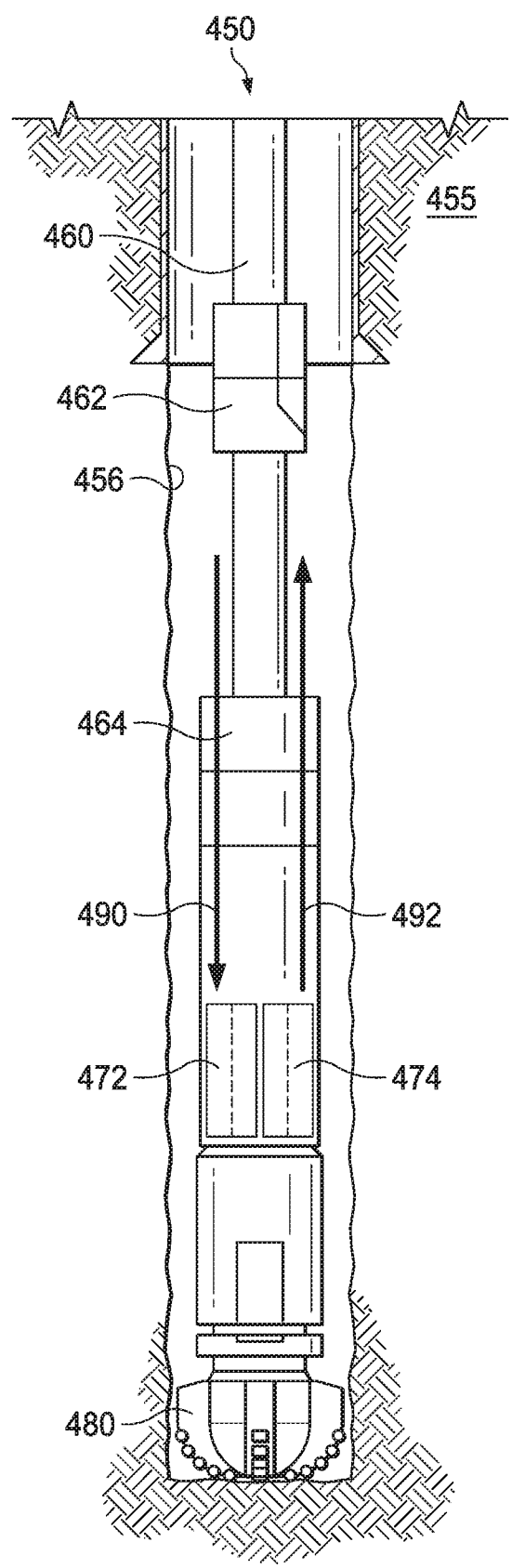
FIG. 4B is an illustration of a diagram of an example LDS analyzation system located at a downhole location within a borehole.

FIG. 4B is an illustration of a diagram of an example LDS analyzation system 450 located at a downhole location within a borehole 456. Borehole 456 is located in a subterranean formation 455. Subterranean formation 455 can be heterogeneous or homogeneous formation types. Borehole 456 can be borehole 110 of FIG. 1.

Inserted into borehole 456 is a drill string 460. Attached to drill string 460 is an optional powered isolation sub 462. Powered isolation sub 462 can electrically isolate the lower portion of drill string 460, and can pass through to the lower attached BHA a portion of the electrical power transmitted through drill string 460. A traditional isolation sub 464 can be located lower on drill string 460 compared to powered isolation sub 462. Traditional isolation sub 464 can provide electrical isolation for the lower attached components. A extracted material collector/preparer 472 and a LDS device/analyzer 474 can be located below traditional isolation sub 464. At the end of drill string 460 is a drill bit 480. Other tools, devices, power supplies, and transceivers can be located on, in, or around drill string 460.

Similar to LDS analyzation system 400, extracted material collector/preparer 472 and LDS device/analyzer 474 can perform the described functions. In this example, the extracted material collector and the extracted material preparer are shown as a single extracted material collector/preparer 472. In some aspects, they can be separate devices, as indicated by the dashed line. The LDS device and the LDS analyzer are shown as a single LDS device/analyzer 474. In some aspects, they can be separate devices, as indicated by the dashed line. In some aspects, the LDS analyzer functions can be performed by other systems, such as surface equipment, e.g., a well site controller or computing system. In some aspects, LDS device/analyzer 474 can include one or more of a GC system, a GC combustion system, a LC system, or a LC combustion system. In some aspects, LDS device/analyzer 474 can include other types of physical-chemical separation techniques.

Instructions and input parameters can be provided by downhole communication 490. Measurements and results can be provided by an uphole communication 492, such as results generated from LDS device/analyzer 474 and a status of the system. Downhole communication 490 and uphole communication 492 can be performed by conventional means.

Figure 5A:
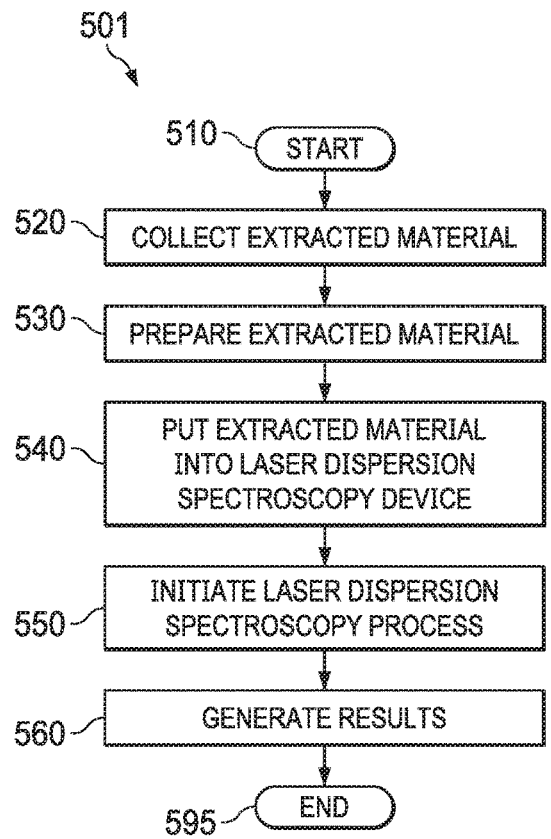
FIG. 5A is an illustration of a flow diagram of an example method utilizing a LDS system at a well site.

FIG. 5A is an illustration of a flow diagram of an example method 501 utilizing a LDS system at a well site. Method 501 can be used to analyze extracted material collected from drilling mud or other fluids pumped up from a borehole. The analysis can be used as inputs into other decision making processes and systems. Method 501 starts at a step 510 and proceeds to a step 520. In the step 520, extracted material can be collected from drilling mud, hydraulic fracturing fluid, chemical fracturing fluid, and other fluids pumped from a borehole. The collection process can vary as different types of extracted material can be handled by separate processes, such as gas extracted material collection being handled differently than solid extracted material collection. In some aspects, the extracted material can be collected at a downhole location where the fluid is not first pumped to a surface location.

Proceeding to a step 530, the extracted material can be prepared. The preparations can be zero or more of separating, draining fluid, cleaning, isolating, adding support material, diluting, filtering, changing to a different phase state or form, combusting, removing moisture, changing pressure, changing flow rate, and other preparation processes. Different types of extracted material can utilize varying preparation techniques, for example, solids can utilize a pulverizing process or variable dilution materials can be utilized.

In a step 540, the prepared extracted material can be moved into a LDS device. There can be more than one LDS device, such as separate devices to conduct analysis of different extracted material phase states, allowing multiple analyses to be generated.

Proceeding to a step 550, the LDS process can be initiated and the measurements collected. The measurements can relate to the composition of the extracted material. In a step 560, the collected measurements can be analyzed to determine one or more characteristics of the extracted material, i.e., results. The results can be communicated to other systems and processes, to users, and be used as inputs to well site operation plans, and other decision processes. Method 501 ends at a step 595.

Figure 5B:
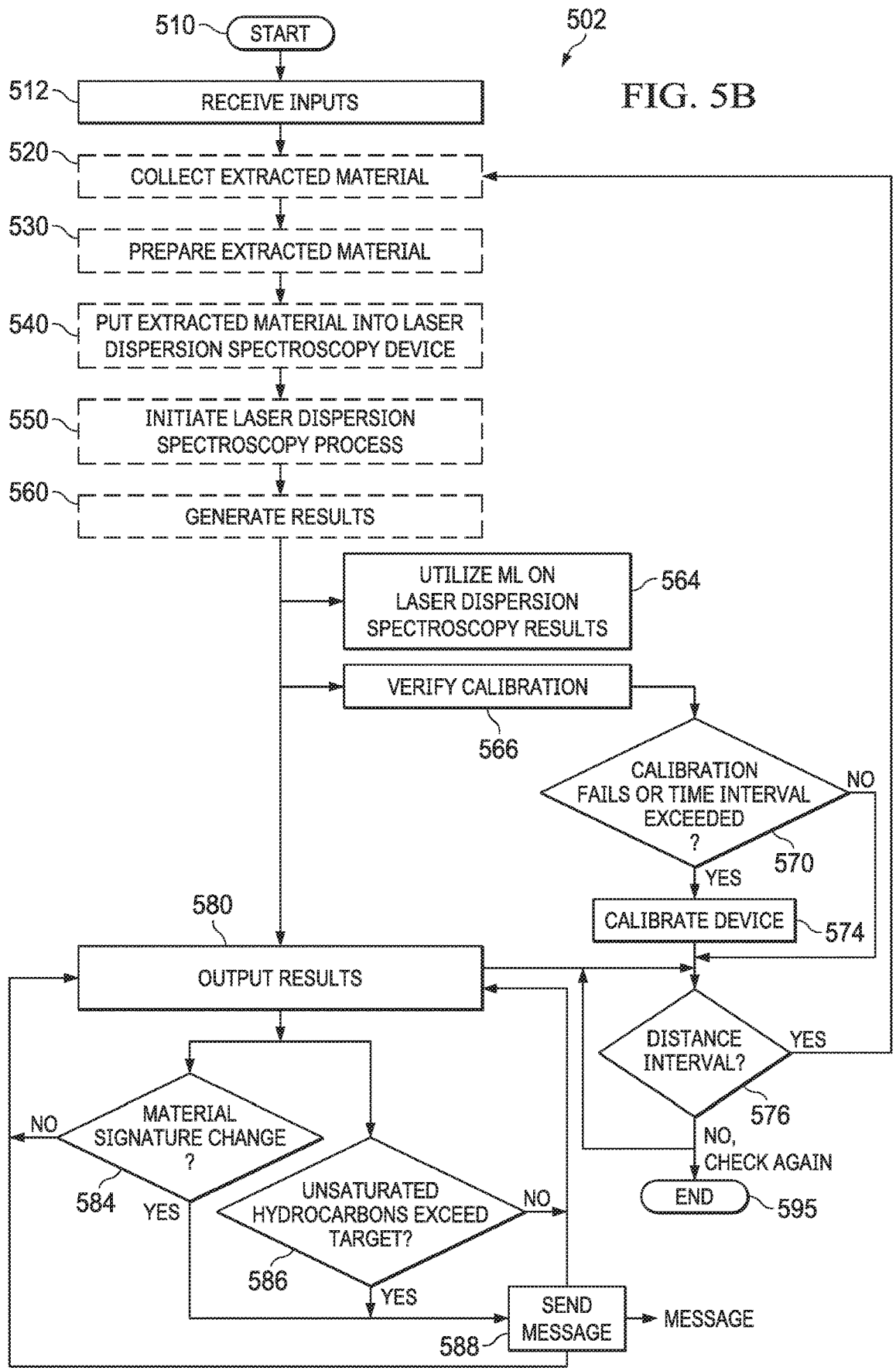
FIG. 5B is an illustration of a flow diagram of an example method, building on FIG. 5A, to perform decision checkpoints.

FIG. 5B is an illustration of a flow diagram of an example method 502, building on FIG. 5A, to perform decision checkpoints. Steps that are similar in method 501 and method 502 are shown using dashed outlines, and steps that are new are shown using solid outlines. Method 502 starts at step 510 and proceeds to a step 512. In step 512, the process can receive one or more inputs. The inputs can be parameters for how to proceed in other steps. The inputs can include a signature change parameter for phase signatures, a signature change parameter for composition signatures, reference peak parameters, e.g., a reference standard parameter, for one or more types of extracted material, a calibration sample parameter indicating the type of calibration to perform, a verification time interval, a calibration time interval, a machine learning algorithm parameter specifying an algorithm to utilize, target unsaturated hydrocarbon parameter, distance parameters between extracted material samples, distance parameters to indicate a length to extrapolate a core sample, parameters regarding the drill bit and fluids utilized downhole, and other input parameters.

Proceeding to step 520, method 502 proceeds through to step 530, step 540, step 550, and step 560. Step 560 can further include a step 564 which can utilize machine learning algorithms, artificial intelligence, and other intelligent systems to extrapolate results generated by the LDS analyzer to generate results that are better suited to the needs of the receivers of the information, such as a user or a well site controller. Step 560 can further include a step 566 to verify the calibration of the LDS device. The verification process can be initiated if an elapsed time is exceeded, such as indicated by the verification time interval. The verification process can compare the results from the extracted material to a reference peak and if the extracted material has a shifted peak by at least the reference peak parameter, a calibration process can be requested.

Proceeding from step 566 is a decision step 570 to determine if the calibration verification failed, or if an elapsed time from the last calibration has exceeded the calibration time interval. If the resultant is "Yes", then method 502 proceeds to a step 574 where a calibration process can be performed using a reference sample. If the resultant is "No", then method 502 proceeds to a decision step 576.

In decision step 576, the process can determine the distance that the well site operations have covered since the previous collection of extracted material as compared to a distance parameter. The distance parameter can be increased proportionately to an extrapolation length of a core sample, such that an extended core sample can be used over a greater distance. For example, the drill bit can move a specified number of inches or feet, or casing can be applied for specified number of feet, e.g., the distance between collecting extracted material. If the resultant of the comparison is that the distance parameter has been met or exceed, i.e., "Yes", method 502 proceeds to step 520 where new extracted material is collected. If the resultant is "No", method 502 can remain at this step until the appropriate distance is covered or until another end state is reached. If an end state is reached, method 502 ends at step 595.

Proceeding from step 560, in a step 580, the results can be communicated, e.g., output, to users, other systems, or other processes. The outputs can be used as inputs to decision processes for the well site. Part of the results outputted by step 580 can include information for two additional decisions steps. In a decision step 584, the signature of extracted material can be compared to a signature generated from a previous iteration, e.g., previous execution, of method 502. In some aspects, the signature can be a phase signature change, for example, a gas turning to a liquid. In some aspects, the signature can be a composition signature change, for example, a change in a ratio of oil to water. The signature change amounts, e.g., the amount of change to derive a "Yes" resultant, can be provided as inputs to the process, such as in step 512. For example, an oil-water ratio can be targeted at least a twenty percent change, or other values can be utilized.

If a "Yes" resultant is determined, then method 502 proceeds to a step 588 where a signature change message can be communicated to a user or system. This can be an alert that a change in downhole conditions can be brought to the attention of a system or user, such as indicating a change in downhole operations. From step 588, method 502 can return to step 580 and follow other paths forward. In decision step 584, a "No" resultant can proceed back to step 580 and proceeds along the other paths from step 580.

In a decision step 586, the detected quantity of unsaturated hydrocarbons, i.e., unsaturated linear hydrocarbons, can be compared to a target unsaturated hydrocarbon parameter, such as received by step 512. If the unsaturated hydrocarbon target is met or exceeded, then the resultant is "Yes" and method 502 proceeds to step 588 where a unsaturated hydrocarbon message can be communicated to a user or system. This can be an alert that a change in downhole conditions can be brought to the attention of a system or a user, and can indicate a change in downhole operations. In decision step 586, a "No" resultant proceeds back to step 580 and proceeds along the other paths from step 580.

The order of steps presented in method 502 is for demonstration purposes. Several steps, such as step 566, step 580, decision step 570, decision step 584, and decision step 586 can be performed in various orders and dependencies between them can be included or extended.

Figure 6:
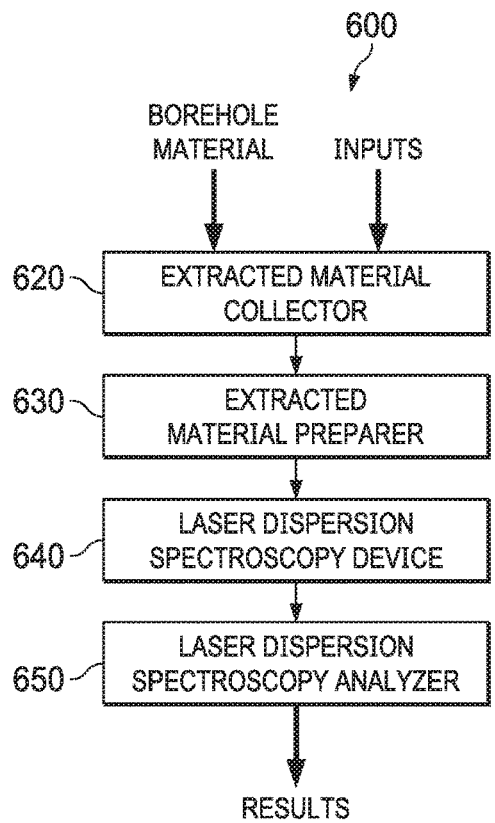
FIG. 6 is an illustration of a block diagram of an example LDS system.

FIG. 6 is an illustration of a block diagram of an example LDS analyzer system 600, which can be implemented as one or more devices. LDS analyzer system 600 can be utilized to analyze extracted material from a borehole to determine composition parameters, unsaturated hydrocarbon parameters, signature change parameters, and other parameters. LDS analyzer system 600 includes an extracted material collector 620, an extracted material preparer 630, a LDS device 640, and a LDS analyzer 650.

LDS analyzer system 600 can receive inputs to direct operations, such as time intervals, target parameters, core samples, calibration references, borehole locations, and distances, selected algorithms to utilize, and other input parameters. The inputs can be received utilizing a conventional transceiver using conventional protocols, e.g., utilizing a data receiver. The received inputs can be received from a data source, such as a database, data file, user input, a well site controller, a reservoir controller, or other data sources.

LDS analyzer system 600 can receive extracted material from borehole material, such as drilling mud, fluids, and other material pumped from a borehole. The borehole material can include cuttings and other material from downhole of a borehole. Extracted material collector 620 can collect extracted material of interest from the borehole material. The extracted material can be prepared by extracted material preparer 630. The preparation can perform various operations depending on the analysis to be conducted and the type of extracted material to be analyzed. Preparation can include cleaning, filtering, separating, isolating, draining fluid, adding material, altering material, and other preparation functions.

The extracted material can be moved into a LDS device 640. LDS device 640 can collect measurements on the extracted material, such as composition or densities. The measurements can be provided to LDS analyzer 650 to analyze the measurements and generate results. LDS analyzer 650 can be implemented as an application, a code library, dynamic link library, function, module, other software implementation, or combinations thereof. In some aspects, LDS analyzer 650 can be implemented in hardware, such as a ROM, a graphics processing unit, or other hardware implementation. In some aspects, LDS analyzer 650 can be implemented partially as a software application and partially as a hardware implementation.

LDS analyzer system 600 can communicate, using a results transmitter, one or more results to another system, such as to a user, a well site controller, a computing system, a downhole tool controller, a well site operation plan system, or other well related system. The well site controller, downhole tool controller, or well site operation plan system can utilize the results to determine future steps or operations, or to adjust plans. The receiving computing system can be included in the computing system where LDS analyzer 650 is executing or be located in another computing system proximate or distance from LDS analyzer system 600. LDS analyzer system 600 can be, or can include, conventional interfaces configured for transmitting and receiving data.

In some aspects, LDS analyzer system 600 can operate partially or fully in serial or parallel mode such that analysis can be conducted on more than one extracted material set at a time, allowing the overall processing time to be reduced. A memory or data storage of LDS analyzer system 600 can be configured to store the processes and algorithms for directing the operation of LDS analyzer system 600.

A portion of the above-described apparatus, systems, or methods may be embodied in or performed by various analog or digital data processors, wherein the processors are programmed or store executable programs of sequences of software instructions to perform one or more of the steps of the methods. A processor may be, for example, a programmable logic device such as a programmable array logic (PAL), a generic array logic (GAL), a field programmable gate arrays (FPGA), or another type of computer processing device (CPD). The software instructions of such programs may represent algorithms and be encoded in machine-executable form on non-transitory digital data storage media, e.g., magnetic or optical disks, random-access memory (RAM), magnetic hard disks, flash memories, and/or read-only memory (ROM), to enable various types of digital data processors or computers to perform one, multiple or all of the steps of one or more of the above-described methods, or functions, systems or apparatuses described herein.

Portions of disclosed examples or embodiments may relate to computer storage products with a non-transitory computer-readable medium that have program code thereon for performing various computer-implemented operations that embody a part of an apparatus, device or carry out the steps of a method set forth herein. Non-transitory used herein refers to all computer-readable media except for transitory, propagating signals. Examples of non-transitory computer-readable media include, but are not limited to: magnetic media such as hard disks, floppy disks, and magnetic tape; optical media such as CD-ROM disks; magneto-optical media such as floppy disks; and hardware devices that are specially configured to store and execute program code, such as ROM and RAM devices. Examples of program code include both machine code, such as produced by a compiler, and files containing higher level code that may be executed by the computer using an interpreter.

In interpreting the disclosure, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

Those skilled in the art to which this application relates will appreciate that other and further additions, deletions, substitutions, and modifications may be made to the described embodiments. It is also to be understood that the terminology used herein is for the purpose of describing particular embodiments only, and is not intended to be limiting, because the scope of the present disclosure will be limited only by the claims. Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, a limited number of the exemplary methods and materials are described herein.

What is claimed is:

1. A method, comprising:
   collecting extracted material from a location in a subterranean formation, wherein the location is proximate a position of hydrocarbon operations within a borehole;
   preparing the extracted material, wherein extraneous material is removed;
   putting the extracted material into a laser dispersion spectroscopy (LDS) device;
   initiating a LDS process utilizing the extracted material; and
   generating results from analyzation of the LDS process, wherein the LDS process utilizes at least one of a gas phase analysis, a liquid phase analysis, or an isotropic analysis, and the extracted material is within pores of downhole material retrieved from the location.

2. The method as recited in claim 1, further comprising:
   outputting the results to one or more of a well site controller, well site operation plan system, or a well site operator.

3. The method as recited in claim 1, wherein the hydrocarbon operation includes at least one of a hydraulic fracturing operation, a chemical fracturing operation, a casing operation, a drilling system, a logging while drilling system, a measuring while drilling system, and seismic while drilling system.

4. The method as recited in claim 1, further comprising repeating the method at a distance parameter, wherein the distance parameter is an input parameter.

5. The method as recited in claim 1, wherein the LDS process further utilizes a solid phase analysis.

6. The method as recited in claim 5, wherein for the solid phase analysis, the preparing further comprises one or more of pulverizing the extracted material, cleaning the extracted material, and draining fluid from the extracted material.

7. The method as recited in claim 1, further comprising:
   determining a composition of the extracted material utilizing a spectral deconvolution process using a reference standard or a machine learning algorithm, and outputting the composition as the results.

8. The method as recited in claim 7, wherein the results include at least one of a mineral composition, an organic composition, or a vitrinite reflectance parameter.

9. The method as recited in claim 1, further comprising:
   comparing a detected quantity of unsaturated linear hydrocarbons and a target quantity of unsaturated hydrocarbons, and outputting an unsaturated hydrocarbon message when the target quantity of unsaturated hydrocarbons is exceeded.

10. The method as recited in claim 1, further comprising:
    ascertaining a phase signature or a composition signature of the extracted material and outputting a signature change message when the respective of the phase signature or of the composition signature changes, utilizing a signature change parameter, from a previous execution of the method.

11. The method as recited in claim 1, further comprising:
    verifying calibration of the LDS device when a selected reference peak shifts or at an end of a specified verification time interval; and
    calibrating the LDS device when the verifying calibration fails or after a specified calibration time interval.

12. The method as recited in claim 1, wherein the LDS process utilizes at least one of a gas phase analysis or an isotropic analysis utilizing a target gas released from the extracted material, or a liquid phase analysis utilizing a target liquid released from the extracted material.

13. The method as recited in claim 12, further comprising:
    prepping the extracted material utilizing one or more of a filtering process, a moisture removal process, a separation process, a pressure control process, a flow control process, or an additional support gases process.

14. The method as recited in claim 12, further comprising:
    converting respective of the target gas or the target liquid to carbon dioxide.

15. The method as recited in claim 12, further comprising:
    diluting respective of the target gas or the target liquid utilizing a variable dilution material.

16. A system to analyze extracted material, extracted from a location within a borehole, comprising:
    an extracted material collector, capable of collecting the extracted material to be analyzed from borehole material;
    an extracted material preparer, capable of receiving the extracted material from the extracted material collector and capable of cleaning, separating, isolating, and altering the extracted material to prepare the extracted material for analysis;
    a laser dispersion spectroscopy (LDS) device, capable of receiving the extracted material from the extracted material preparer and capable of performing a LDS process on the extracted material; and
    a LDS analyzer, capable of producing results from an output of the LDS device, wherein the LDS process utilizes at least one of a gas phase analysis, a liquid phase analysis, or an isotropic analysis, and the extracted material is within pores of downhole material retrieved from the location.

17. The system as recited in claim 16, wherein the system is located downhole proximate to a hydrocarbon operation.

18. The system as recited in claim 16, wherein the extracted material collector collects the extracted material from drilling mud, hydraulic fracturing fluid, or chemical fracturing fluid.

19. The system as recited in claim 16, wherein the extracted material preparer is further capable of converting gas to carbon dioxide, pulverizing the extracted material that is a solid, diluting the extracted material, and draining fluid from the extracted material.

20. The system as recited in claim 16, wherein the LDS device is one of a LDS gas phase device, a LDS liquid phase device, a LDS solid phase device, or a LDS isotropic device.

21. The system as recited in claim 16, wherein the results from the LDS analyzer comprise one or more of a mineral composition, an organic composition, a molecular composition, a calibration parameter of the LDS device, or a status of the system.

22. The system as recited in claim 16, further comprising:
    a data receiver, capable of receiving inputs, wherein the inputs are one or more of a verification time interval, a calibration time interval, a reference peak parameter for one or more types of extracted material, the location within the borehole, a reference standard parameter, a machine learning algorithm parameter, or a reference standard, and wherein the LDS analyzer utilizes the inputs to direct operation of the LDS device and to produce the results.

23. The system as recited in claim 16, further comprising:
a results transmitter, capable of communicating the results to a second system, wherein the second system is one or more of a well site controller, a well site operation plan system, a user, a well operator, a downhole tool controller, a data center, a computing system, or a cloud environment.

24. The system as recited in claim 16, further comprising:
a physical-chemical separation device, capable of producing second results utilized by the LDS analyzer using the extracted material, wherein the physical-chemical separation device is located proximate the LDS device and is one or more of a gas chromatography (GC) system, a GC combustion system, a liquid chromatography (LC) system, or a LC combustion system.

25. A computer program product having a series of operating instructions stored on a non-transitory computer-readable medium that directs a data processing apparatus when executed thereby to perform operations to analyze extracted material, the operations comprising:
directing a collecting of extracted material from a location in a subterranean formation, wherein the location is proximate a position of hydrocarbon operations within a borehole;
instructing a preparing of the extracted material, wherein extraneous material is removed;
initiating a putting of the extracted material into a laser dispersion spectroscopy (LDS) device;
executing a LDS process utilizing the extracted material;
generating results from an analysis of the LDS process; and
communicating the results to one or more other systems, wherein the LDS process utilizes at least one of a gas phase analysis, a liquid phase analysis, or an isotropic analysis, and the extracted material is within pores of downhole material retrieved from the location.

* * * * *